(12) United States Patent
Larke

(10) Patent No.: US 7,342,060 B2
(45) Date of Patent: Mar. 11, 2008

(54) PROCESS FOR MANUFACTURE OF PENTAERYTHRITOL DIPHOSPHITES

(75) Inventor: Carroll W. Larke, Zoar, OH (US)

(73) Assignee: Dover Chemical Corporation, Dover, OH (US)

( * ) Notice: Subject to any disclaimer, the term of this patent is extended or adjusted under 35 U.S.C. 154(b) by 497 days.

(21) Appl. No.: 10/707,402

(22) Filed: Dec. 11, 2003

(65) Prior Publication Data

US 2005/0131244 A1    Jun. 16, 2005

(51) Int. Cl.
*C07F 9/6578* (2006.01)
*C08K 5/527* (2006.01)

(52) U.S. Cl. .......................... 524/120; 558/78; 568/12

(58) Field of Classification Search ................... 568/12; 558/78; 524/120
See application file for complete search history.

(56) References Cited

U.S. PATENT DOCUMENTS

| | | | |
|---|---|---|---|
| 5,364,895 A | 11/1994 | Stevenson et al. | |
| 5,438,086 A * | 8/1995 | Stevenson et al. | .......... 524/120 |
| 5,674,927 A | 10/1997 | Mahood | |
| 6,613,823 B1 | 9/2003 | Battiste et al. | |
| 6,656,887 B2 | 12/2003 | Yagishita et al. | |
| 6,657,025 B2 | 12/2003 | Blackmon et al. | |
| 6,657,032 B2 | 12/2003 | Vanderbilt | |

FOREIGN PATENT DOCUMENTS

WO    WO 03/102004 A1    12/2003

* cited by examiner

*Primary Examiner*—Rebecca Anderson
*Assistant Examiner*—Andrew B. Freistein
(74) *Attorney, Agent, or Firm*—Buckingham Doolittle & Burroughs LLP; Louis F. Wagner

(57) ABSTRACT

A method is disclosed for the production of pentaerythritol diphosphites of high spiro isomer content. The pentaerythritol diphosphites are produced via sequential transesterification of pentaerythritol with a monophosphite followed by a substituted phenol or other alcohol, wherein the transesterification reactions are carried out under controlled conditions of temperature and pressure. The unique reaction conditions result in intermediate and final pentaerythritol diphosphites of high spiro isomer content and high total yield of the diphosphites.

82 Claims, No Drawings

PROCESS FOR MANUFACTURE OF PENTAERYTHRITOL DIPHOSPHITES

BACKGROUND OF INVENTION

The present invention is directed to a process for the manufacture of spiro pentaerythritol diphosphites. More specifically, the present invention is directed to a process for the manufacture of pentaerythritol diphosphites via transesterification under vacuum to produce a diphosphite with high spiro isomer content.

Pentaerythritol diphosphites comprise at least two isomeric forms, the spiro and caged isomers. The commercial desirability of the spiro isomer over the caged isomer is well known. It is, therefore, desirable to produce pentaerythritol diphosphites having high spiro isomer content.

Generally, pentaerythritol diphosphites can be prepared by at least two different methods. In one method, two sequential transesterification reactions are performed, first, the reaction of pentaerythritol with triphenyl phosphite to make diphenyl pentaerythritol diphosphite, and second, the reaction of the intermediate diphenyl pentaerythritol diphosphite with the appropriate alkylphenol or alcohol to produce the desired pentaerythritol diphosphite. In another method, dichloropentaerythritol diphosphite is reacted with the appropriate alkylphenol or alcohol to produce the desired pentaerythritol diphosphite. The latter method is said to produce a bis(alkylphenyl) pentaerythritol diphosphite with a negligible portion of caged isomer but involves more complex and expensive processing technology. The former transesterification method is cheaper to implement but generally produces mixtures of isomers having a spiro isomer content of from 50 percent upon to 75 percent depending on the method of preparation and the reactants. Thus bis (alkylphenyl) pentaerythritol diphosphite prepared via transesterification typically are mixtures of spiro and caged isomers that must be further purified by selective crystallization in order to produce a predominantly spiro product. Such an approach, however, inherently leads to a relatively low yield.

One approach to improving the spiro isomer content of bis (2,4-di-t-butylphenyl) pentaerythritol diphosphite produced via transesterification is to react diphenyl pentaerythritol diphosphite (DPPEDP) with 2,4-di-t-butylphenol in a $C_{10}$-$C_{16}$ n-alkane or cycloalkane solvent. This method gives a product with a spiro isomer content of up to 90 percent, but the diphosphite yield is relatively low at about 77 percent.

An economically more favorable and thus desirable transesterification process would be one which produces a bis (alkylphenyl) pentaerythritol diphosphite with a spiro isomer content of at least 90 percent, and with a high diphosphite yield of at least 95 percent.

SUMMARY OF INVENTION

It is therefore an object of the present invention to provide a method for the production of pentaerythritol diphosphites via transesterification chemistry having a high spiro isomer content and high yield.

In general, the present invention provides a process for producing bis(alkylphenyl) pentaerythritol diphosphites with high spiro isomer content greater than 90 percent via transesterification chemistry with yields greater than 95 percent. The process of this invention comprises conventional transesterification reactions where the increase in the spiro isomer content and yield results from: (1) unique reaction conditions used to produce an intermediate product and the final product that minimize competing reaction products; and (2) the use of distillation to concentrate the diphosphite content of the intermediate and final products.

Accordingly, it is an object of the present invention to disclose a sequence of transesterification reactions which maximize the spiro content of a pentaerythritol diphosphite.

It is another object of the present invention to effect the above sequence of transesterification reactions in a preferred embodiment using pentaerythritol and triphenyl phosphite to form an intermediate pentaerythritol diphosphite followed by a second transesterification reaction with a substituted phenol or lower alcohol to produce a high spiro content pentaerythritol diphosphite.

These and other objects of the present invention will become more readily apparent from a reading of the following detailed description and with further reference to the appended claims.

DETAILED DESCRIPTION

The process of the present invention involves sequential transesterification reactions to provide an intermediate and final reaction product. The first reaction is the transesterification of pentaerythritol (formula 1)

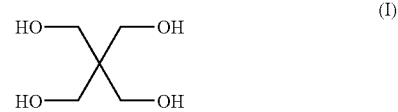

with a monophosphite in the presence of an alkaline catalyst. The monophosphite can be selected from the group of triaryl phosphites, e.g., triphenyl phosphite (formula II)

or trialkyl phosphites, e.g., trimethyl phosphite, or triethylphosphite.

More generically, a trialkyl or triaryl phosphite may be shown as $P—(OR^1)_3$ wherein $R^1$ is selected from the group consisting straight-chain or branched alkyl groups, cycloaliphatic groups which may have substituents, straight-chain or branched alkenyl groups, unsubstituted or alkyl-substituted aryl groups and arylalkyl groups.

Specific non-limiting examples of straight-chain or branched alkyl groups are $C_{1-20}$ alkyls, e.g., methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl and stearyl groups.

Specific non-limiting examples of the cycloaliphatic or cyclic alkyl groups which may have substituents are cycloalkyl groups having 5 to 7 carbon atoms such as cyclopentyl, cyclohexyl and cycloheptyl groups, and the alkylcycloalkyl groups having 6 to 11 carbon atoms wherein the position of the alkyl group may vary, such as methylcyclopentyl, dimethylcyclopentyl, methylethylcyclopentyl, dimethylcyclopentyl, methylcyclohexyl, dimethylcyclohexyl, methylethylcyclohexyl, diethylcyclohexyl, methylcycloheptyl, dimethylcycloheptyl, methylcycloheptyl, and diethylcycloheptyl groups.

Specific non-limiting examples of the straight-chain or branched alkenyl groups are those having 2 to 30 carbon atoms wherein the position of the double bond may vary, such as butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, and octadecenyl groups.

Specific examples of the unsubstituted or alkyl-substituted aryl groups are the aryl groups having 6 to 18 carbon atoms such as phenyl, diphenyl and naphthyl groups, and alkylaryl groups having 7 to 40 carbon atoms wherein the alkyl group may be straight-chain or branched and may be bonded to any position on the aryl group, such as tolyl, xylyl, ethylphenyl, propylphenyl, butylphenyl, pentylphenyl, hexylphenyl, heptylphenyl, octylphenyl, nonylphenyl, decylphenyl, undecylphenyl, dodecylphenyl, diethylphenyl, dibutylphenyl and dioctylphenyl groups. The alkylaryl groups may additionally have substituents including functional groups such as alkoxy, hydroxy, cyano, nitro, halides, carboxylic acids, etc.

Specific examples of the arylalkyl groups are those having 7 to 40 carbon atoms wherein the alkyl group may be straight-chain or branched, such as benzyl, phenylethyl, phenylpropyl, phenylbutyl, phenylpentyl and phenylhexyl groups.

This first transesterification results in the production of an intermediate pentaerythritol diphosphite reaction product having spiro isomer shown in the following base formula (III):

$$R^1-O-P\diagup\diagdown O-R^1 \qquad (III)$$

wherein $R^1$ is as previously defined and caged isomer shown in the following formula (IV):

$$\begin{array}{c}(IV)\end{array}$$

In a preferred embodiment, pentaerythritol is transesterified with triphenyl phosphite to produce the intermediate diphenyl pentaerythritol diphosphite shown in the following formula (V):

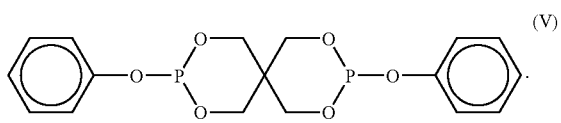

The second reaction is the transesterification of the intermediate pentaerythritol diphosphite with an alcohol, $R^2OH$ wherein the alcohol is selected from the group consisting of $C_8$ alkanols, $C_8$ alkenols, phenols and derivatives thereof, $C_{7-40}$ alkylaryl phenols and derivatives thereof and $C_{7-40}$ arylalkyl phenols and derivatives thereof, wherein said derivatives are chemical moieties selected from the group consisting of halogens, $C_{1-4}$ alkyls, $C_{1-4}$ alkoxy compounds, amino groups, $C_{1-6}$ carboxylic acid groups, cyano groups, nitro groups, etc., in the presence of an alkaline catalyst to produce a pentaerythritol diphosphite of the following formula (VI):

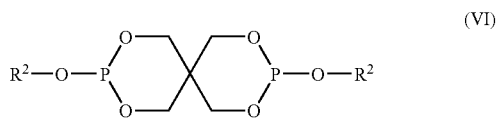

where $R^2$ is preferably selected from the group consisting of 2,4-di-t-butylphenyl, 2,4-dicumylphenyl, and lower $C_8$ $C_{20}$ alkanes, e.g., stearyl, isodecyl and decyl derived preferably from alcohols are selected preferably from the group consisting of 2,4-di-t-butylphenol, 2,4-dicumylphenol of formula (VII),

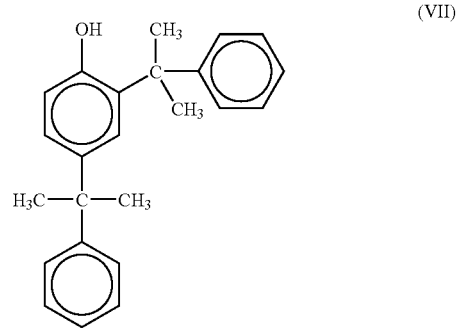

and more generically as described previously.

In a preferred embodiment, in the second transesterification reaction, the diphenyl pentaerythritol diphosphite intermediate from the first transesterification reaction of this invention is transesterified with 2,4-dicumylphenol in the presence of an alkaline catalyst to produce bis(2,4-dicumylphenyl) pentaerythritol diphosphite with high yield and a high spiro isomer content as shown in the following formula (VIII):

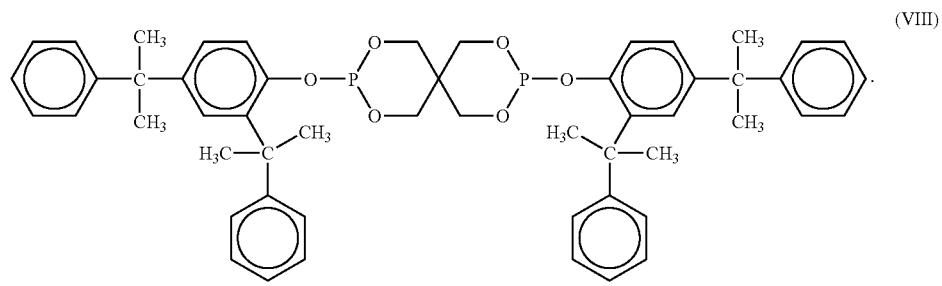 (VIII)

In preparing a reaction mixture for the first esterification reaction, monophosphite and pentaerythritol are used in a ratio of approximately 1 to 3 moles of monophosphite per mole of pentaerythritol. In the preferred embodiment of the first transesterification reaction, a stoichiometric amount of 2 moles monophosphite per mole of pentaerythritol is used. A solvent may be used in the reaction mixture to reduce the viscosity, aid reactivity and/or to enable subsequent purification via fractional crystallization of the reaction mixture. Therefore, a solvent is not required and is thus optional. When employed, solvents that can be used include aromatic, aliphatic, and cyclic hydrocarbons in the $C_6$ to $C_{24}$ range. Suitable solvents are normal or cyclic paraffins. More particularly, the solvent will be a saturated hydrocarbon or mixture of saturated hydrocarbons selected from the group consisting of $C_6$-$C_{24}$ n-alkanes and cyclo-alkanes. Representative examples of suitable hydrocarbons are n-decane, n-dodecane, n-tridecane, n-hexadecane and the like, and the cyclic and polycyclic analogs such as cyclododecane, bicyclo[4,4,0]decane (decahydronaphthalene) and the like. Often, the solvent will be a solvent mixture and include lower alkanes, e.g., hexane, heptane and cyclohexane. Unsaturated solvents are also useful in the invention, e.g., benzene and toluene. Solvents, if used in the reaction mixture are used in an amount ranging from about 10 weight percent up to about 200 weight percent based on the weight of intermediate pentaerythritol diphosphite produced.

An alkaline catalyst is also used in the first esterification reaction. The alkaline catalyst is preferably an alkaline inorganic compound and most preferably is an alkali or alkaline earth metal oxide, hydroxide, carbonate or alcoholate, all of which are catalysts well-known in the art as being useful for these purposes. The alkaline catalyst is used in the reaction mixture in an amount ranging from about 0.1 weight percent to about 5 weight percent, based on the weight of intermediate pentaerythritol diphosphite produced.

The first transesterification reaction is carried out under controlled conditions of temperature and pressure. In a preferred embodiment of the first transesterification, the reaction is carried out at atmospheric pressure. The reaction can also be carried out under vacuum (full vacuum to about 200 mm Hg) with liberated phenol removed via distillation. The temperature of the first reaction is in a range of between about 60° C. and a final temperature of below 125° C., preferably between 70° C. to about 105° C. At these temperatures the formation of undesirable side reaction products is minimized and correspondingly the yield of pentaerythritol diphosphite is maximized.

While not wishing to be bound to any particular theory, it is believed that the stoichiometry and low temperature of the first transesterification reaction at atmospheric pressure selectively promotes the formation of the spiro and caged isomers of the intermediate diphenyl pentaerythritol diphosphite at the expense of other undesirable side reaction products. The transesterification byproduct is separated from any residual reactants, and side reaction products by distillation or by fractional crystallization of the diphosphite in solvent. This unique processing results in the combined weight of the spiro and caged isomers of the intermediate pentaerythritol diphosphite representing a yield of greater than 95%, based on the monophosphite reactant.

In a preferred embodiment of the first transesterification reaction, phenol is produced by the transesterification of pentaerythritol and triphenyl phosphite in the presence of alkaline catalyst to form diphenyl pentaerythritol diphosphite as the intermediate pentaerythritol diphosphite. The liberated phenol, any unreacted monophosphite and any side reaction products are removed by distillation. The distillation is performed with a temperature in the range of about 100° C. to about 300° C., and a pressure of about full vacuum to about 200 mm Hg. The phenol byproduct and monophosphite reactants are of high quality and can be used as raw material for other reactions. The side reaction components can be recycled into subsequent first transesterification reactions as they rearrange to spiro and caged pentaerythritol diphosphites.

Other methods of purification of the first reaction mixture include fractional crystallization in solvent and fractional melt crystallization. If the reaction is run in solvent, the same solvent used for dilution of the reaction mixture can be used for the fractional crystallization of the pentaerythritol diphosphites.

Following the first transesterification reaction, the purified intermediate pentaerythritol diphosphite produced is used in a second transesterification reaction to form a second pentaerythritol diphosphite. In preparing the second transesterification reaction mixture, a substituted phenol or alcohol and the intermediate pentaerythritol diphosphite are used in amounts ranging from approximately stoichiometric to an excess of about 300 weight percent of the stoichiometric amount of the substituted phenol or alcohol. The substituted phenol (or alcohol in excess, if used) is used to reduce the viscosity of the second reaction mixture and to bias the reaction to completion. In the preferred embodiment, the substituted phenol is 2,4-dicumyl phenol or 2,4-di-t-butyl phenol. Thus, when a substituted phenol is used, the second pentaerythritol diphosphite formed during the second transesterification reaction can be a bis(substituted phenol) pentaerythritol diphosphite.

A solvent may be used in the reaction mixture to reduce viscosity, aid reactivity, and/or to enable subsequent reaction mass purification via fractional crystallization. But a solvent is not required and is thus optional. Solvents that can be used include aromatic, aliphatic, and cyclic hydrocarbons in the 6-24 carbon range. Normal or cyclic paraffins are suitable solvents. More particularly, the solvent will be a saturated hydrocarbon or mixture of saturated hydrocarbons selected from a group consisting of 6 to 24 carbon n-alkanes and cyclo-alkanes. Representative examples of suitable hydrocarbons are n-decane, n-dodecane, n-tridecane, n-hexadecane and the like; and the cyclic and polycyclic analogs such as cyclododecane, bicyclo[4,4,0]decane (decahydronaphthalene) and the like. Often, the solvent will be a solvent mixture and include lower alkanes, e.g., hexane, heptane, and cyclohexane. Unsaturated solvents are also useful in the invention, e.g., benzene, toluene and the like. Solvents if used in the reaction mixture, are used in an amount ranging from about 10 weight percent to about 200 weight percent based on the weight of pentaerythritol diphosphite produced.

An alkaline catalyst is also used in the second esterification reaction. The alkaline catalyst is preferably an alkaline inorganic compound and most preferably is an alkali or alkaline earth metal oxide, hydroxide, carbonate, alcoholate, all of which are catalysts well-known in the art as being useful for these purposes. The alkaline catalyst is used in the second reaction mixture in an amount ranging from about 0.1 weight percent to about 5 weight percent, based on the weight of the second pentaerythritol diphosphite produced.

The second transesterification reaction is carried out under controlled conditions of temperature and pressure. The temperature of the second reaction mixture is maintained in a range of about 120° C. to below 175° C., preferably 120° C. to 170° C. and preferably is maintained at about 150° C. The reaction is performed under vacuum to give a pressure in the range of about full vacuum to about 200 mm Hg absolute. In the preferred embodiment, phenol is produced by the transesterification of diphenyl pentaerythritol diphosphite intermediate and 2,4-dicumyl phenol to form bis(2,4-dicumylphenyl) pentaerythritol diphosphite as the second pentaerythritol diphosphite. The byproduct phenol that is liberated during the second transesterification reaction is removed by distillation. The phenol byproduct is of high quality and can be used as raw material for other reactions.

While not wishing to be bound by a particular theory, it is believed that the stoichiometry, removal of byproduct phenol during the second transesterification reaction, along with the high purity of the pentaerythritol diphosphite, selectively promotes the formation of the spiro isomer of the second pentaerythritol diphosphite at the expense of the caged isomer. The unique reaction conditions during the second transesterification reaction, along with those of the first transesterification reaction result in a spiro isomer content greater than 90% of the combined total weight of the spiro and caged isomers of the second pentaerythritol diphosphite produced in the second transesterification reaction. The total combined weight of the spiro and caged isomers of the second pentaerythritol diphosphite represents a yield of greater than 95%, based on the intermediate pentaerythritol diphosphite reactant.

Following the second transesterification reaction, the second pentaerythritol diphosphite produced is separated form the second reaction mixture via distillation. In the preferred embodiment, the second reaction mixture is distilled to remove any unreacted materials, excess substituted phenol (or alcohol if used), solvent (if used), and/or any residual phenol to leave a purified second pentaerythritol diphosphite that is preferably 99% by weight of spiro and caged isomers of the second pentaerythritol diphosphite, based on the total weight of the second pentaerythritol diphosphite and residual impurities. The distillation is performed with a temperature in the range of about 100° C. to about 300° C., and a pressure of about full vacuum to about 200 mm Hg absolute. In a preferred embodiment, the second pentaerythritol diphosphite is bis(2,4-dicumylphenyl) pentaerythritol diphosphite.

Other methods of purification of the second reaction mass include fractional crystallization and fractional melt crystallization. If solvent crystallization is used to purify the second transesterification reaction mass, the same solvent used for dilution of the reaction mass can be used for the crystallization fractionation process. Solvents that can be used include aromatic, aliphatic, and cyclic hydrocarbons in the 6 to 24 carbon range. Normal or cyclic paraffins are suitable solvents. More particularly, the solvent will be a saturated hydrocarbon or mixture of saturated hydrocarbons selected from a group consisting of 6 to 24 carbon n-alkanes and cycloalkanes. Representative examples of suitable hydrocarbons are n-decane, n-dodecane, n-tridecane, n-hexadecane and the like; and the cyclic and polycyclic analogs such as cyclododecane, bicyclo[4,4,0]decane (decahydronaphthalene) and the like. Often, the solvent will be solvent mixture and include lower alkanes, e.g., hexane and cyclohexane. Unsaturated solvents are also useful in the invention, e.g., benzene, toluene and the like. Solvents if used in the reaction mixture, are used in an amount ranging from about 10 weight percent up to about 200 weight percent based on the weight of pentaerythritol diphosphite produced.

EXAMPLES

The best mode for carrying out the invention will now be described for the purposes of illustrating the best mode known to the applicant at the time. The examples are illustrative only and not meant to limit the invention, as measured by the scope and spirit of the claims.

Example 1

Preparation of Bis-2,4-Dicumyl Pentaerythritol Diphosphite

The transesterification reaction of monopentaerythritol and triphenylphosphite (TPP) is carried out with stoichiometric amounts of TPP and pentaerythritol with a solvent in the presence of an alkaline catalyst at temperatures beginning at 70° C. and ending at less than 125° C., preferably 105-120° C. at atmospheric pressure. Phenol produced during the reaction is removed through vacuum distillation at from 100-300° C. and pressures ranging between 0.01 and 100 mm Hg absolute with greater than 95% of theory recovered and less than 5% remaining in the reaction mass. Unreacted materials remain in this intermediate product at a level typically below 1%, preferably below 0.1%. The phenol byproduct is of high quality and can be used as a raw material in other reactions. Surprisingly, under these conditions, the spiro isomer of DPPEDP is produced in preference to the caged isomer and DPPEDP yields are greater than 95% based on TPP. Solvent is not essential to the reaction chemistry serving only to reduce viscosity and thus is optional. Solvents that can be used include various aromatic hydrocarbons and hydrocarbon solvents in the 6 to 20 carbon range. Alkaline catalyst loading is 0.01-5% by weight of DPPEDP produced. Solvent, if used, can be added to the reaction system in the amount of 10-200% by weight of DPPEDP produced. The reaction scheme and operating parameters produce a reaction crude with DPPEDP with a spiro content of greater than 90%, solvent if used, along with trace amounts of TPP, phenol, and caged isomer of DPPEDP.

The purified high spiro DPPEDP is stable and can be stored molten or solidified or sold as an intermediate product. The stripped TPP, trace phenol and/or solvent is recycled into subsequent DPPEDP production. The next step is to transesterify the high spiro DPPEDP with 2,4-dicumyl phenol to produce high spiro bis-2,4-dicumyl pentaerythritol diphosphite.

High spiro DPPEDP form the previous reaction is added to alkaline catalyzed 2,4-dicumyl phenol at about 150° C. The alkaline catalyst level is 0.1-5% by weight of bis-2,4-dicumyl pentaerythritol diphosphite produced. The reactants can be added in amounts ranging from stoichiometric (2 moles 2,4-dicumyl phenol to 1 mole diphenyl pentaerythritol diphosphite) to large stoichiometric excesses (300% or more to reduce viscosity) of 2,4-dicumyl phenol. A vacuum of 0.01 to 100 mm Hg absolute is maintained to distill the phenol produced in the transesterification reaction to trace levels. The reaction produces bis-2,4-dicumyl pentaerythritol diphosphite that has a spiro isomer content of greater than 90% with phosphite yields (based on DPPEDP) of greater than 95%. The phenol byproduct is of high quality and can be used as a raw material in other processes.

The reaction mass is then stripped via thin film distillation at 150-300° C. and 0.01 to 50 mm Hg absolute to remove the excess 2,4-dicumyl phenol to levels below 0.5%. The resulting products is greater than 90% spiro bis-2,4-dicumylphenyl pentaerythritol diphosphite that can be pastilled, pelletized, or flaked, etc., to the desired product form The distilled 2,4-dicumyl phenol and trace phenol is recycled to subsequent reactions. By employing the reaction parameters described above, the final diphosphite reaction product may be used without the need to resort to recrystallization purification.

The high spiro isomer content pentaerythritol diphosphites made by the methods of the current invention may be used to stabilize any of the polymers known in the art, such as polyolefins, polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Additionally included would be mixtures of different polymers, such as polyphenylene ether/styrenic resin blends, polyvinylchloride/ABS or other impact modified polymers, such as methacrylonitrile containing ABS, and polyester/ABS or polyester plus some other impact modifier may also be used. Such polymers are available commercially or may be made by means well known in the art. However, the diphosphites of the invention are particularly useful in thermoplastic polymers, such as polyolefins, polycarbonates, polyesters, polyphenylene ethers thermoplastic polymers, such as polyolefins, polycarbonates, polyesters, polyphenylene ethers and styrenic polymers, due to the extreme temperatures at which the thermoplastic polymers are often processed and/or used.

Polymers of monoolefins and diolefins, for example would include polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example mixtures of polypropylene with polyisobutylene, polypropylene with polyethylene (for example PP/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethyl pentene, ethylene/heptene, ethylene/octene, propylene/butadiene, isobutylene/isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene-propylene copolymers, LDPE/EVA, LDPE/EAA, LLDPE/EVA and LLDPE/EAA.

Thermoplastic polymers may also include styrenic polymers, such as polystyrene, poly-(p-methylstyrene), poly(α-methylstyrene), copolymers of styrene, p-methylstyrene or alpha-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methacrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene. Styrenic polymers may additionally or alternatively include graft copolymers of styrene or alpha-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures of the styrenic copolymers indicated above.

Nitrile polymers are also useful. These include homopolymers and copolymers of acrylonitrile and its analogs such as methacrylonitrile, such as polyacrylonitrile, acrylonitrile/butadiene polymers, acrylonitrile/alkyl acrylate polymers, acrylonitrile/alkyl methacrylate/butadiene polymers, acrylonitrile/butadiene/styrene (ABS), and ABS which includes methacrylonitrile.

Polymers based on acrylic acids, such as acrylic acid, methacrylic acid, methyl methacrylate acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homopolymers and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinylacetate copolymer, vinyl chloride-ethylene copolymer, vinyl chloride propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acid and diols and/or from hydroxycarboxylic acids or the corresponding lactones, such as polyethylene terephthalate, polybutylene terephthalate, poly-1,4-dimethyliol-cyclohexane terephthalate, poly-[2,2,4-(4-hydroxyphenyl)-propane] terephthalate and polyhydroxybenzoates as well as block copolyetheresters derived from polyethers having hydroxyl end groups.

Polyamides and copolyamides which are derived from diamines and dicarboxylic acids and/or from aminocarboxylic acids or the corresponding lactams, such as polyamide-4, polyamide-6, polyamide-6/6, polyamide-6/10, polyamide-6/9, polyamide-6/12, polyamide-4/6, polyamide-11, polyamide-12, aromatic polyamides obtained by condensation of m-xylene, diamine and adipic acid; polyamides prepared from hexamethylene diamine and isophthalic and/or terephthalic acid and optionally an elastomer as modifier, for example, poly-2,4,4-trimethylhexamethylene terephthalamide or poly-m-phenylene isophthalamide may be useful. Further copolymers of the aforementioned polyamides with poly-olefins, olefin copolymers, ionomers or chemically bonded or grafted elastomers; or with polyethers, such as for instance, with polyethylene glycol, polypropylene glycol or polytetramethylene glycols, and polyamides or copolyamides modified with EPDM or ABS may be used.

The resulting stabilized polymer compositions comprising the phosphites made by the process of this invention may optionally also contain various conventional additives, such as the following:

(1) Antioxidants (1.1) Alkylated monophenols, for example: 2,6-di-t-butyl-4-methylphenol, 2-t-butyl-4,6-dimethylphenol, 2,6-di-t-butyl-4-ethylphenol, 2,6-di-t-butyl-4-n-butylphenol,2,6-di-t-butyl-4-butyl phenol, 2,6-di-cyclopentyl-4-methylphenol, 2-(α-methylcyclohexyl)-4,6-dimethyl phenol, 2,6-d i-octadecyl-4-methylphenol, 2,4,6-tri-cyclohexylphenol, and 2,6-di-t-butyl-4-methoxymethylphenol.

(1.2) Alkylated hydroquinones, for example, 2,6-di-t-buty7l-4-methoxyphenol, 2,5-di-t-butyl-hydroquinone, 2,5-di-t-amyl-hydroquinone, and 2,6-diphenyl-4-octadecyloxyphenol.

(1.3) Hydroxylated thiodiphenyl ethers, for example,2,2'-thio-bis-(6-t-butyl-4-methyl phenol), 2,2'-thio-bis-(4-octylphenol), 4,4'-thio-bis-(6-t-butyl-3-methylphenol), and 4,4'-thio-bis-(6-t-butyl-2-methyl phenol).

(1.4) Alkylidene-bisphenols, for example,2,2'-methylene-bis-(6-t-butyl-4-methylphenol), 2,2'-methylene-bis-(6-t-butyl-4-ehtylphenol), 2,2'-methylene-bis-[4-methyl-6-(alpha-methylcyclohexyl)phenol], 2,2'-methylene-bis-(4-methyl-6-cyclohexylphenol), 2,2'-methylene-bis-(6-nonyl-4-methylphenol), 2,2'-methylene-bis-[6-α-methylbenzyl)-4-nonylphenol], 2,2'-methylene-bis-[6-(α, α-dimethylbenzyl)-4-nonylphenol], 2,2'-methylene-bis-(4,6-di-t-butylphenol), 2,2'-methylene-bis-(4,6-di-t-butylphenol), 4,4'-methylene-bis-(6-t-butyl-2-methylphenol), 1,1-bis-(5-t-butyl-4-hydroxy-2-methylphenyl)butane, 2,6-di-(3-t-butyl-5-methyl-2-hydroxybenzyl)-4-methylphenol, 1,1,3-tris-(5-t-butyl-4-hydroxy-2-methylphenyl)butane, 1,1-bis-(5-t-butyl-4-hydroxy-2-methylphenyl)-3-dodecylmercaptobutane, ethylenglycol-bis-[3,3-bis-(3'-t-butyl-4-hydroxy-phenyl)-butyrate], di-(3-t-butyl-4-hydroxy-5-methylphenyl)-dicyclopentadiene, and di-[2-(3'-t-butyl-2'-hydroxy-5'methylbenzyl)-6-t-butyl-4-methylphenyl]terephthalate.

(1.5) Benzyl compounds, for example, 1,3,5-tris-(3,5-di-t-butyl-4-hydroxybenzyl)-2,4,6-trimethylbenzene,bis(3,5-di-t-butyl-4-hydroxybenzyl)sulfide, isooctyl-3,5-di-t-butyl-4-hydroxybenzyl-mercapto-acetate, bis-(4-t-butyl-3-hydroxy-2,6-dimethylbenzyl)dithiolterephthalate, 1,3,5 tris-(3,5-di-t-butyl-4-hydroxybenzyl)isocyanurate, 1,3,5-tris(4-t-butyl-3-hydroxy-2,6-dimethylbenzyl)isocyanurate, dioctadecyl-3,5-di-t-butyl-4-hydroxybenzyl-phosphonate, calcium salt of monoethyl3,5-di-t-butyl-4-hydroxybenzylphosphonate, and 1,3,5-tris-1,3,5-dicyclohexyl-4-hydroxybenzyl)isocyanurate.

(1.6) Acylaminophenols, for example, 4-hydroxy-lauric acid anilide, 4-hydroxy-stearic acid anilide, 2,4-bis-octylmercapto-6-(3,5-t-butyl-4-hydroxy-anilino)-s-triazine, and octyl-N-(3,5-di-t-butyl-4-hydroxyphenyl)-carbanate (1.7) Esters of β-(3,5-di-t-butyl-4-hydroxyphenyl)-propionic acid with monohydric or polyhydric alcohols, for example, methanol, diethyleneglycol, octadecanol, triethyleneglycol, 1,6-hexanediol, pentaeryth ritol, neopentyiglycol, tris-hydroxyethyl isocyanurate, thiodiethyleneglycol, and di-hydroxyethyl oxalic acid diamide.

(1.8) Esters of β-(5-t-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentyglycol, trishydroxyethyl isocyanurate, thiodiethyleneglycol, and di-hydroxyethyl oxalic acid diamide.

(1.9) Esters of β-(5-t-butyl-4-hydroxy-3-methylephenyl) propionic acid with mono- or polyhydric alcohols, e.g. with methanol, di-ethylene glycol, octadecanol, triethylene glycol, 1,6-hexanediol, pentaerythritol, neopentyl glycol, tris (hydroxyethyl)isocyanurate, thiodiethylene glycol, and N,N"-bis(hydroxyethyl)oxalic acid diamide.

(1.10) Amides of β-(3,5-di-t-butyl-4-hydroxyphenyl)-propionic acid, for example, N,N"-di-(3,5-di-t-butyl-4-hydroxyphenylpropionyl)-hexamethylendiamine, N,N"-di-(3,5-di-t-butyl-4-hydroxyphenylpropionyl)-trimethylendiamine, and N,N"-di-(3,5-di~t~butyl-4-hydroxyphenylpropionyl).hydrazine (2) UV Absorbers and Light Stabilizers.

(2.1) 2-(2"-Hydroxyphenyl)-benzotriazoles, for example, the 5"-methyl-, 3',5'-di-t-butyl-, 5'-t-butyl-, 5'-(1,1,3,3-tetramethylbutyl)-, 5-chloro-3',5'-di-t-butyl-, 5-chloro-3'-t-butyl-5'-methyl-, 3'-sec-butyl-5'-t-butyl-, 4'-octoxy, 3',5'-di-t-amyl-, and 3',5'-bis-(α,α-dimethyl benzyl)-derivatives.

(2.2) 2-Hydroxy-benzophenones, for example, the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy.

(2.3) Esters of substituted and unsubstituted benzoic acids, for example, phenyl salicylate, 4-t-butyl-phenylsalicilate, octylphenyl salicylate, dibenzoylresorcinol, bis-(4-t-butylbenzoyl)-resorcinol, benzoylresorcinol, 2,4-di-t-butyl-phenyl-3,5-di-t-butyl-4-hydroxybenzoate and hexadecyl-3,5-di-t-butyl-4-hydroxybenzoate.

(2.4) Acrylates, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, α-carbomethoxy-p-methoxy-cinnamic acid methyl ester, and N-(β-carbomethoxy-β-cyano-vinyl)-2-methyl-indoline.

(2.5) Nickel compounds, for example, nickel complexes of 2,2"-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-t-butylbenzylphosphonic acid monoalkyl esters, such as of the methyl, ethyl or butyl ester, nickel complexes of ketoximes such as of 2-hydroxy-4-methylpentyl undecyl ketoxime, and nickel complexes of 1-phenyl-4-lauroyl-5-hydroxy-pyrazol, optionally with additional ligands.

(2.6) Sterically hindered amines, for example bis(2,2,6,6-tetramethylpiperidyl)-sebacate, bis(1,2,2,6,6-pentamethylpiperidyl)-sebacate, n-butyl-3,5-di-t-butyl-4-hydroxybenzyl malonic acid, bis-(1,2,2,6,6-pentamethylpiperidyl)ester, condensation product of 1-hydroxyethyl-2,2,6,6-tetramethyl-4-hydroxy-piperidine and succinic acid, condensation product of N,N"-(2,2,6,6-tetramethylpiperidyl)-hexamethylendiamine and 4-t-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1"-(1,2-ethanediyl)-bis-(3,3,5,5-tetramethylpiperazinone). Such amines include hydroxylamines derived from hindered amines, such as di-(1-hydroxy-2,2,6,6-tetramethylpipefldifl-4-yl) sebacate; 1-hydroxy-2,2,6,6-tetramethyl-4-benzoxypiperidine; 1-hydroxy-2,2,6,6-tetramethyl-4(3,5-di-t-butyl-4-hydroxyhydrocinnamoyloxy) piperidine; and N-(1-hydroxy-2,2,6,6-tetramethylpiperidin-4-yl)-ε-caprolactam.

(2.7) Oxalic acid diamides, for example, 4,4"-di-octyloxy-oxanhlide, 2,2"-di-octyloxy-5,5-di-t-butyl-oxanilide, 2,2"-di-dodecyloxy-5,5"-di-t-butyl-oxanilide, 2-ethoxy-2"-ethyl-oxanilide, N,N"-bis(3-dimethylaminopropyl)-oxalamide, 2-ethoxy-5-t-butyl-2"-ethyloxanilide and its mixture with 2-ethoxy-2"-ethyl-5,4"-di-t-butyloxanilide and mixtures of o-methoxy and p-methoxy as well as of o-ethoxy and p-ethoxy disubstituted oxanilides.

(3) Metal deactivators, for example, N,N"-diphenyloxalic acid diamide, N-salicylal-N"-salicyloylhydrazine, N,N"-bis-salicyloylhydrazine, N,N"-bis-(3,5-di-t-butyl-4-hydroxyphenylpropionyl)-hydrazine, salicyloylamino-1,2,4-triazole, bis-benzyliden-oxalic acid dihydrazide.

(4) Phosphites and phosphonites, for example triphenyl phosphite, diphenylalkyl phosphites, phenyldialkyl phosphites, tris(nonyl-phenyl) phosphite, trilauryl phosphite, trioctadecyl phosphite, distearyl pentaerythritol diphosphite, tris(2,4-di-t-butylphenyl)phosphite, diisodecyl pentaerythritol diphosphite, bis(2,4-di-t-butylphenyl)pentaerythritol diphosphite, tristearyl sorbitol triphosphite, and tetrakis(2,4-di-t-butylphenyl) 4,4"-biphenylene diphosphonite.

(5) Peroxide scavengers, for example esters of β-thiodipropioniC acid, for example the lauryl, stearyl, myristyl or tridecyl esters, mercaptobenzimidazole or the zinc salt of 2-mercaptobenzimidazole, zinc-dibutyl-ditbiocarbamate, dioctadecyldisulfide, pentaerythritol-tetrakis(β-dodecylmercapto)-propionate.

(6) Polyamide stabilizers, for example copper salts in combination with iodides and/or phosphorus compounds and salts of divalent manganese.

(7) Basic co-stabilizers, Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, barium stearate, magnesium stearate, sodium ricinoleate, potassium palmitate, antimony pyrocatecholate and zinc pyrocatecholate.

(8) Nucleating agents, for example, 4-t-butyl-benzoic acid, adipic acid, diphenylacetic acid.

(9) Fillers and reinforcing agents, for example, calcium carbonate, silicates, glass fibers, asbestos, talc, kaolin, mica, barium sulfate, metal oxides and hydroxides, carbon black, graphite.

(10) Aminoxvpropanoate derivatives such as methyl-3-[N,N-dibenzylaminoxy]propanoate; ethyl-3-[N,N-dibenzylaminoxy]propanoate; 1,6-hexamethylene-bis[3-(N,N-dibenzylaminoxy)propanoate]; methyl-[2-(methyl)-3(N,N-dibenzylaminoxy)propanoate]; octade-cyl-3-[N,N-dibenzylaminoxy]propanoic acid; tetrakis[(N,N-dibenzylaminoxy) ethyl carbonyl oxymethyl]methane; octadecyl-3-[N,N-diethylaminoxy]propanoate; 3-[N,N-dibenzylaminoxy] propanoic acid potassium salt; and 1,6-hexamethylene bis [3-(N-allyl-N-dodecyl aminoxy)propanoate].

(11) Other additives, for example, plasticizers, lubricants, emulsifiers, pigments, optical brighteners, flame-proofing agents, anti-static agents, blowing agents and thiosynergists such as dilaurylthiodipropionate or distearylthiodipropionate.

Hindered phenolic antioxidants may also be present in the polymer composition. Use of bis(alkylpheny)l pentaerythritol diphosphites of the present invention may result in enhanced polymer protection by reducing the formation of color resulting from the presence of the phenols. Such phenolic antioxidants include in addition to those specifically mentioned previously, n-octadecyl-3,5-di-t-butyl-4-hydroxyhydrocinnamate, neopentaneterayl tetrakis-(3,5-di-t-butyl-4-hydroxyl-hydrocinnamate), di-n-octade-cyl-3,5-di-t-butyl-4-hydroxybenzyl-phosphonate, 1,3,5-tris(3,5-di-t-butyl-4-hydroxybenzyl-)isocyanurate, thiodiethylene-bis (3,5-di-t-butyl-4-hydroxyhydrocinnamate), 1,3,5-trimethyl-2,4,6-tris(3,5-di-t-butyl-4-hydroxybenzyl)benzene, 3,6-dioxaoctamethylene bis(3-methyl-5-t-butyl-4-hydroxyhydrocinnamate), 2,6-di-t-butyl-p-cresol, 2,2'-ethylidene-bis(4,6-di-t-butylphenol), 1,3,5-tris-(2,6-dimethyl-4-t-butyl-3-hydroxybenzyl)isocyanurate, 1,1,3-tris-(2-methyl-4-hydroxy-5-t-butylphenyl)butane, 1,3,5-tris[2-(3,5-di-t-butyl-4-hydroxyhydrocinnainoloxy)-ethyl]-isocyanurate, 3,5-di-(3,5-di-t-butyl-4-hydroxybenzyl)-mesitol, hexamethylene-bis(3,5-di-t-butyl-4-hydroxyhydrocimiamate), 1-(3,5-di-t-butyl-4-hydroxyanilino)-3,5-di(octylthio)-s-triazine, N,N"-hexamethylene-bis(3,5-di-t-butyl-4-hydroxyhydrocinnamamide), calcium bis(ethyl-3,5-di-t-butyl-4-hydroxybenzylphosphonate), ethylene bis[3,3-di(3-t-butyl-4-hydroxyphenyl)butyrate], octyl 3,5-di-t-butyl-4-hydroxybenzylmercaptoacetate,bis(3,5-di-t-butyl-4-hydroxyhydrocinnamoyl(hydrazide, and N,N'-bis-[2-(3,5-t- butyl-4-hydroxyhydroxocinnamoyl oxy)-ethyl]-oxamide, and preferablyneopentanetetraylte-trakis(3,5-di-t-butyl-4-hydroxyhydrocinnamate), n-octadecyl-3,5-di-t-butyl-4-hydroxyhydrocinnamate, 1,3,5-trimethyl-2,4,6-tris(3,5-di-t-butyl-4-hydroxy-benzyl)benzene, 1,3,5-tris-(3,5-di-t-butyl-4-hydroxybenzyl)isocyanurate, 2,6-di-t-butyl-p-cresol or 2,2'-ethylidene-bis(4,6-di-t-butylphenol).

(12) Lactones, for example, 5,7-di-t-butyl-3-phenyl-3H-benzofuran-2-one; 5,7-di-cumyl-3-phenyl-3H-benzofuran-2-one; nonyl-e-phenyl-3H-benzofuran-2-one; dinonyl-3-phenyl-3H-benzofuran-2-one; 5-t-butyl-3-phenyl-3H-benzofuran-2-one; 5-cumyl-3-phenyl-3H-benzofuran-2-one; and octyl-3-phenyl-3H-benzofuran-2-one, and other 3-arylbenzofuran-2-ones.

Other additives, such as oxazaphospholidines, may additionally or alternatively be present. Likewise, the instant compounds prevent color formation when hindered amine light stabilizers are present, such hindered amines including-bis(1,2,2,6,6-pentamethyl-4-piperidyl)$_2$-n-butyl-2-(3,5-di-t-butyl-4-hydroxy-benzyl) malonate; bis(2,2,6,6-tetramethyl-4-piperidyl) sebacate; dimethyl-succinate polymer with 4-hydroxy-2,2,6,6-tetramethyl-1-piperidinethanol; and polymers of 2,4-dichloro-6-octylamino-s-triazine with N'-(2,2,6,6-tetramethyl-4-piperidyl)hexamethylene diamine.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A method for synthesizing pentaerythritol diphosphites comprising the steps of:

(a) transesterifying pentaerythritol of formula (I)

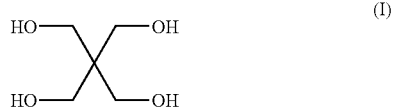

with a monophosphite of formula P—(OR$^1$)$_3$ to form a first reaction mixture which comprises an intermediate pentaerythritol diphosphite having a spiro isomer as shown in the following formula (III),

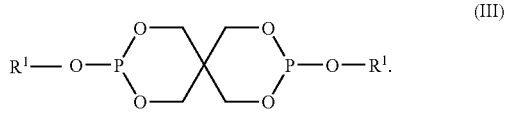

a caged isomer shown in the following formula (IV),

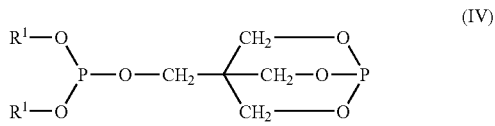

unreacted monophosphite and side reaction products wherein R$^1$ is selected from the group consisting of straight-chain or branched C$_{1-20}$ alkyl groups, C$_{5-7}$ cycloaliphatic groups, straight-chain or branched C$_{2-30}$ alkenyl groups, C$_{6-18}$ aryl groups, C$_{7-40}$ alkylaryl groups and C$_{7-40}$ arylalkyl groups;

(b) removing reaction products by distillation other than said intermediate pentaerythritol diphosphite from said first reaction mixture; and (c) transesterifying said intermediate pentaerythritol diphosphite with an alcohol selected from the group consisting of C$_{8-22}$ alkanols, C$_{8-22}$ alkenols, phenols, C$_{7-40}$ alkylaryl alcohols and C$_{7-40}$ arylalkyl alcohols to form a second reaction mixture which comprises a final pentaerythritol diphosphite of formula (VI)

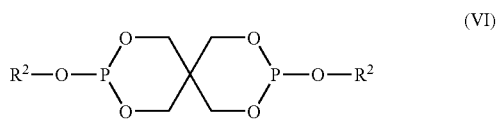

where R$^2$ is selected from the group consisting of C$_{8-22}$ alkyls, C$_{8-22}$ alkenyls, phenyl, C$_{7-40}$ alkylaryls and C$_{7-40}$ arylalkyls.

2. The method of claim 1 which further comprises the step of separating said intermediate pentaerythritol diphosphite from said first reaction mixture to produce a purified intermediate pentaerythritol diphosphite.

3. The method of claim 2 wherein said monophosphite is selected from the group consisting of trimethyl phosphite, triethyl phosphite and triphenyl phosphite.

4. The method of claim 3 wherein said monophosphite is triphenyl phosphite.

5. The method of claim 4 wherein said intermediate pentaerythritol diphosphite is diphenyl pentaerythritol diphosphite.

6. The method of claim 1 wherein a ratio of said monophosphite to said pentaerythritol is about 2 moles of monophosphite per mole of pentaerythritol.

7. The method of claim 1 which further comprises an alkaline catalyst in said first transesterification step (a).

8. The method of claim 7, wherein said amount of said alkaline catalyst ranges from about 001 weight percent to about 5 weight percent, based on the intermediate pentaerythritol diphosphite.

9. The method of claim 1 wherein said alcohol is 2,4-dicumyl phenol.

10. The method of claim 1, wherein said first transesterification reaction pressure is in a range from about 001 mm Hg to about 100 mm Hg.

11. The method of claim 10 wherein said first transesterification reaction temperature is in a range from about 70° C. to about 105° C.

12. The method of claim 11 wherein said first reaction mixture further comprises a solvent.

13. The method of claim 12, wherein said solvent is selected from the group consisting of C$_6$-C$_{20}$ aromatic hydrocarbons and C$_6$-C$_{20}$ aliphatic hydrocarbons and blends thereof.

14. The method of claim 13, wherein said solvent is added in an amount ranging from about 10 weight percent to about 200 weight percent of said intermediate pentaerythritol diphosphite.

15. The method of claim 11 wherein said intermediate pentaerythritol diphosphite comprises a spiro isomer content of greater than 90 percent.

16. The method of claim 15 wherein said intermediate pentaerythritol diphosphite has a yield of greater than 95 percent, based on the pentaerythritol.

17. The method of claim 2 wherein said separating step comprises distillation of said reaction mixture sufficient to purify said intermediate pentaerythritol diphosphite to a purity of at least 99 percent.

18. The method of claim 17 wherein the purity of said intermediate pentaerythritol diphosphite is at least 999 percent.

19. The method of claim 2 further comprising the step of separating said second pentaerythritol diphosphite from said second reaction mixture.

20. The method of claim 19 wherein said step of separating said second pentaerythritol diphosphite from said second reaction mixture comprises a step of distillation.

21. The method of claim 19 wherein said alcohol is selected from the group consisting of 2,4-di-t-butylphenol and 2,4-dicumylphenol.

22. The method of claim 21 wherein said alcohol is 2,4-dicumylphenol.

23. The method of claim 19 wherein said final pentaerythritol diphosphite is selected from the group consisting of bis(2,4-dicumylphenyl) pentaerythritol diphosphite and bis(2,4-di-t-butylphenyl) pentaerythrltol diphosphite.

24. The method of claim 19 wherein a temperature of said second transesterification reaction in step (c) is in a range of about 120° C. to about 170° C.

25. The method of claim 24 wherein pressure of said second transesterification reaction in step (c) is in a range of about 001 mm Hg to about 100 mm Hg.

26. The method of claim 19, wherein the amount of said alcohol ranges from about 2 moles to about 8 moles per mole of said intermediate pentaerythritol diphosphite.

27. The method of claim 19, which further comprises an alkaline catalyst in said second transesterification reaction in step (c).

28. The method of claim 27, wherein the amount of said alkaline catalyst is in a range of about 0.01 weight percent to about 5 weight percent, based on the final pentaerythritol diphosphite.

29. The method of claim 19, wherein said final pentaerythritol diphosphite comprises a spiro isomer content of greater than 90 mole percent.

30. A method for synthesizing pentaerythritol diphosphites comprising the steps of:
(a) transesterifying pentaerythritol with a monophosphite to form a first reaction mixture which comprises an intermediate pentaerythritol diphosphite and unreacted monophosphite and side reaction products at a temperature below 125° C.;
(b) removing reaction products by distillation other than said intermediate pentaerythritol diphosphite from said first reaction mixture; and
(c) transesterifying said intermediate pentaerythritol diphosphite with an excess of an alcohol to form a second reaction mixture which comprises a final pentaerythritol diphosphite at a temperature below 175° C., said final pentaerythritol diphosphite having a spiro content in excess of 90 mole percent without purification by recrystallization.

31. The method of claim 30 which further comprises the step of separating said intermediate pentaerythritol diphosphite from said first reaction mixture to produce a purified intermediate pentaerythritol diphosphite.

32. The method of claim 31 wherein said monophosphite is selected from the group consisting of trimethyl phosphite, triethyl phosphite and triphenyl phosphite.

33. The method of claim 32 wherein said monophosphite is triphenyl phosphite.

34. The method of claim 33 wherein said intermediate pentaerythritol diphosphite is diphenyl pentaerythritol diphosphite.

35. The method of claim 30 wherein a ratio of said monophosphite to said pentaerythritol is about 2 mores of monophosphite per mole of pentaerythritol.

36. The method of claim 30 which further comprises en alkaline catalyst in said first transesterification reaction in step (a).

37. The method of claim 30, wherein said amount of said alkaline catalyst ranges from about 001 weight percent to about 5 weight percent, based on the intermediate pentaerythritol diphosphite.

38. The method of claim 30 wherein said alcohol is 2,4-dicumyl phenol.

39. The method of claim 30, wherein a reaction pressure of said first transesterification reaction in step (a) is in a range from about 001 mm Hg to about 100 mm Hg.

40. The method of claim 39 wherein a reaction temperature of said first transesterification reaction in step (a) is in a range from about 70° C. to about 150° C.

41. The method of claim 40 wherein said first reaction mixture further comprises a solvent.

42. The method of claim 41, wherein said solvent is selected from the group consisting of $C_8$-$C_{20}$ aromatic hydrocarbons and $C_8$-$C_{20}$ aliphatic hydrocarbons and blends thereof.

43. The method of claim 42, wherein said solvent is added in an amount ranging from about 10 weight percent to about 200 weight percent of said intermediate pentaerythritol diphosphite.

44. The method of claim 30 wherein said intermediate pentaerythritol diphosphite comprises a spiro isomer content of greater than 90 percent.

45. The method of claim 44 wherein said intermediate pentaerythritol diphosphite has a yield of greater than 95 percent, based on the pentaerythritol.

46. The method of claim 31 wherein said separating step comprises distillation of said reaction mixture sufficient to purify said intermediate pentaerythritol diphosphite to a purity of at least 99 percent.

47. The method of claim 46 wherein the purity of said intermediate pentaerythritol diphosphite is at least 99.9 percent.

48. The method of claim 31 further comprising the step of separating said second pentaerythritol diphosphite from said second reaction mixture.

49. The method of claim 48 wherein said step of separating said second pentaerythritol diphosphite from said second reaction mixture comprises a step of distillation.

50. The method of claim 48 wherein said alcohol is selected from the group consisting of 2,4-di-t-butylphenol and 2,4-dicumylphenol.

51. The method of claim 50 wherein said alcohol is 2,4-dicumyiphenol.

52. The method of claim 48 wherein said final pentaerythritol diphosphite is selected from the group consisting of bis(2,4-dicumylphenyl) pentaerythritol diphosphite and bis(2,4-di-t-butylphenyl) pentaerythritol diphosphite 53. The method of claim 48 wherein a temperature of said second transesterification reaction of step (c) is in a range of about 120° C. to about 170° C.

54. The method of claim 53 wherein a pressure of said second transesterification reaction of step (c) is in a range of about 0.01 mm Hg to about 100 mm Hg.

55. The method of claim 48, wherein the amount of said alcohol ranges from about 2 moles to about 8 moles per mole of said intermediate pentaerythritol diphosphite.

56. The method of claim 48, which further comprises a second alkaline catalyst in said second transesterification reaction of step (c).

57. The method of claim 56, wherein the amount of said alkaline catalyst is in a range of about 0.01 weight percent to about 5 weight percent, based on the final pentaerythritol diphosphite.

58. The method of claim 48, wherein said final pentaerythritol diphosphite comprises a spiro isomer content of greater than 90 mole percent.

59. A method for synthesizing bis(2,4-dicumylphenyl) pentaerythritol diphosphite comprising the steps of:
(a) transesterifying pentaerythritol of formula (I)

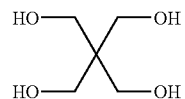
(I)

with triphenyl phosphite of formula (II)

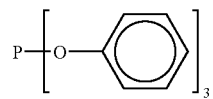
(II)

to form an intermediate reaction mixture comprising diphenyl pentaerythritol diphosphite of formula (V)

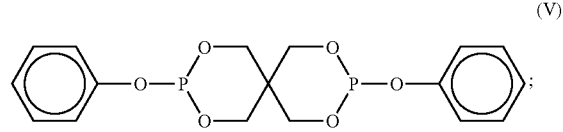
(V)

(b) removing phenol and reaction products by distillation other than diphenylpentaerythritol diphosphite from said intermediate reaction mixture;

(c) transesterifying said intermediate pentaerythritol diphosphite with 2,4-dicumyl phenol of formula (VII)

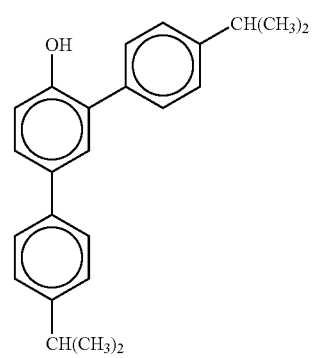
(VII)

to form a second reaction mixture which comprises a final pentaerythritol diphosphite bis(2,4-dicumyiphenyl) pentaerythritol diphosphite of formula (VIII)

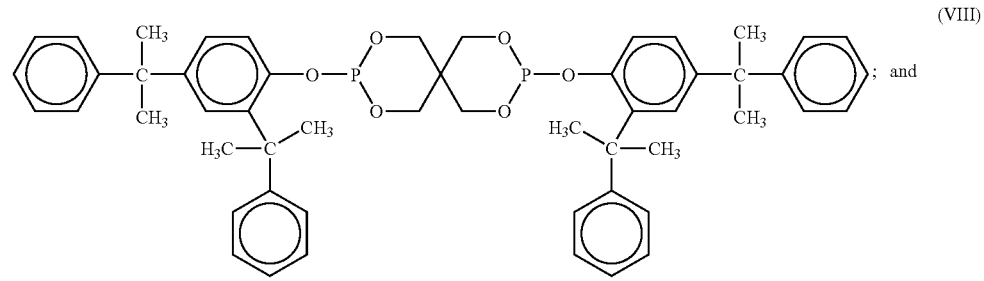
(VIII); and (d) removing phenol from said second reaction mixture.

60. The method of claim 59 wherein a ratio of said triphenyl phosphite to said pentaerythritol is about 2 moles of triphenyl phosphite per mole of pentaerythritol.

61. The method of claim 59 which further comprises an alkaline catalyst for said first transesterification reaction in step (a).

62. The method of claim 61, wherein said amount of said alkaline catalyst ranges from about 001 weight percent to about 5 weight percent, based on the intemiediate diphenyl pentaerythritol diphosphite.

63. The method of claim 62, wherein said first transesterification reaction pressure is in a range from about 001 mm Hg to about 100 mm Hg.

64. The method of claim 63 wherein said first transesterification reaction temperature is in a range from about 70° C. to about 105° C.

65. The method of claim 64 wherein said first reaction mixture further comprises a solvent.

66. The method of claim 65, wherein said solvent is selected from the group consisting of $C_6$-$C_{20}$ aromatic hydrocarbons and $C_6$-$C_{20}$ aliphatic hydrocarbons and blends thereof.

67. The method of claim 66, wherein said solvent is added in an amount ranging from about 10 weight percent to about 200 weight percent of said intermediate diphenyl pentaerythritol diphosphite.

68. The method of claim 67 wherein said intermediate diphenyl pentaerythritol diphosphite comprises a spiro isomer content of greater than 90 percent.

69. The method of claim 68 wherein said intermediate diphenyl pentaerythritol diphosphite has a yield of greater than 95 percent, based on the pentaerythritol.

70. The method of claim 59 wherein said step of removing phenol from said first reaction mixture by distillation.

71. The method of claim 70 wherein said step of removing phenol from saId reaction mixture purifies said intermediate diphenyl pentaerythritol diphosphite to a purity of at least 99 percent.

72. The method of claim 71 wherein the purity of said intermediate diphenyl pentaerythritol diphosphite is at least 99 9 percent.

73. The method of claim 70 wherein said step of removing phenol from said second reaction mixture by distillation.

74. The method of claim 73 wherein a temperature of said second transesterification reaction of step (c) is in a range of about 120° C. to about 170° C.

75. The method of claim 74 wherein a pressure of said second transesterification reaction of step (c) is in a range of about 0 01 mm Hg to about 100 mm Hg.

76. The method of claim 75, wherein the amount of said 2,4-dicumyl phenol ranges from about 2 moles to about 8 moles per mole of said intermediate diphenyl pentaerythritol diphosphite.

77. The method of claim 76, which further comprises a second alkaline catalyst for said second transesterification step.

78. The method of claim 77, wherein the amount of said second alkaline catalyst is in a range of about 001 weight percent to about 5 weight percent, based on the bis(2,4-dicumylphenyl) pentaerythritol diphosphite.

79. The method of claim 78, wherein said final bis(2,4-dicumylphenyl) pentaerythritol diphosphite comprises a spiro isomer content of greater than 90 mole percent.

80. The method of claim 1 in which said first and second transesterification reactions are performed without a solvent.

81. The method of claim 30 in which said first and second transesterification reactions are performed without a solvent.

82. The method of claim 59 in which said first and second transesterification reactions are performed without a solvent.

\* \* \* \* \*

UNITED STATES PATENT AND TRADEMARK OFFICE
CERTIFICATE OF CORRECTION

PATENT NO. : 7,342,060 B2  Page 1 of 1
APPLICATION NO. : 10/707402
DATED : March 11, 2008
INVENTOR(S) : Carroll W. Larke It is certified that error appears in the above-identified patent and that said Letters Patent is hereby corrected as shown below:

At column 11, line 63, replace "buty7l-4-methoxyphenol" with --butyl-4-methoxyphenol--.

In claim 18, column 17, line 9, replace "999" with --99.9--.

In claim 59, column 19, line 35, replace "trlphenyl" with --triphenyl--.

In claim 72, column 22, line 2, replace "99 9" with --99.9--.

In claim 75, column 22, line 12, replace "0 01" with --0.01--.

Signed and Sealed this

First Day of July, 2008

JON W. DUDAS
*Director of the United States Patent and Trademark Office*